United States Patent
Huang et al.

(10) Patent No.: US 12,376,730 B1
(45) Date of Patent: Aug. 5, 2025

(54) METHOD, SYSTEM, AND DEVICE FOR REMOVING SMOKE FROM LAPAROSCOPE IMAGES BASED ON CONDITIONAL DIFFUSION MODEL

(71) Applicant: Shandong Normal University, Shandong (CN)

(72) Inventors: Pu Huang, Shandong (CN); Dengwang Li, Shandong (CN); Jie Xue, Shandong (CN); Yao Cheng, Shandong (CN); Bin Jin, Shandong (CN); Haitao Niu, Shandong (CN); Guangyong Zhang, Shandong (CN); Xiangyu Zhai, Shandong (CN); Hao Li, Shandong (CN); Baolong Tian, Shandong (CN); Linchuan Nie, Shandong (CN)

(73) Assignee: Shandong Normal University, Shandong (CN)

( * ) Notice: Subject to any disclaimer, the term of this patent is extended or adjusted under 35 U.S.C. 154(b) by 0 days.

(21) Appl. No.: 18/985,040

(22) Filed: Dec. 18, 2024

(30) Foreign Application Priority Data

Jan. 29, 2024 (CN) .......................... 202410115722.5

(51) Int. Cl.
*A61B 1/00* (2006.01)
*A61B 1/313* (2006.01)
(Continued)

(52) U.S. Cl.
CPC .. *A61B 1/000095* (2022.02); *A61B 1/000096* (2022.02); *A61B 1/3132* (2013.01);
(Continued)

(58) Field of Classification Search
None
See application file for complete search history.

(56) References Cited

U.S. PATENT DOCUMENTS 10,803,555 B2 * 10/2020 Song .................... G06N 3/048
10,832,091 B2 * 11/2020 Sen ...................... G06F 18/214
(Continued)

FOREIGN PATENT DOCUMENTS

| CN | 114638767 | 6/2022 |
|---|---|---|
| CN | 116664450 | 8/2023 |

*Primary Examiner* — James A Thompson
(74) *Attorney, Agent, or Firm* — JCIPRNET

(57) ABSTRACT

Disclosed are a method, system, and device for removing smoke from laparoscope images based on a conditional diffusion model. The method includes: segmenting a video of a laparoscopic surgery according to the number of frames to form a data set; performing smoke rendering on the obtained laparoscope smokeless images, and synthesizing paired smoky images to obtain a synthetic data set containing the smokeless images and the smoky images; inputting the smokeless images into the conditional diffusion model for forward noise addition, and continuously adding noise until the smokeless images are completely noised; inputting the smoky images into a smoke sensing module to obtain smoke concentration and position information, then training a neural network, and continuously performing reverse denoising on the completely noised images using the trained neural network until clear smokeless images are outputted; and optimizing a smoke removal model through a multi-loss function fusion strategy.

6 Claims, 4 Drawing Sheets

(51) Int. Cl.
*G06T 5/20* (2006.01)
*G06T 5/50* (2006.01)
*G06T 5/60* (2024.01)
*G06T 5/70* (2024.01)
*G06T 5/92* (2024.01)
*G06T 7/00* (2017.01)
*G06T 7/11* (2017.01)
*G06T 7/174* (2017.01)
*G06T 11/00* (2006.01)

(52) U.S. Cl.
CPC ............... *G06T 5/20* (2013.01); *G06T 5/50* (2013.01); *G06T 5/60* (2024.01); *G06T 5/70* (2024.01); *G06T 5/92* (2024.01); *G06T 7/0014* (2013.01); *G06T 7/11* (2017.01); *G06T 7/174* (2017.01); *G06T 11/00* (2013.01); *G06T 2207/10016* (2013.01); *G06T 2207/20076* (2013.01); *G06T 2207/20084* (2013.01); *G06T 2207/20182* (2013.01); *G06T 2207/30004* (2013.01); *G06T 2210/41* (2013.01)

(56) References Cited

U.S. PATENT DOCUMENTS

| | | | |
|---|---|---|---|
| 2023/0047937 A1* | 2/2023 | Gubbi Lakshminarasimha | G06T 5/60 |
| 2023/0122835 A1* | 4/2023 | Maske | G06T 7/0012 382/167 |
| 2023/0377097 A1* | 11/2023 | Li | G06T 7/11 |
| 2024/0037950 A1* | 2/2024 | Zhu | G06T 5/50 |
| 2024/0161388 A1* | 5/2024 | Luo | G06T 7/596 |
| 2024/0171788 A1* | 5/2024 | Kreis | H04N 21/234363 |
| 2025/0097439 A1* | 3/2025 | Westcott | H04N 19/172 |

* cited by examiner

Segment a video of a laparoscopic surgery according to the number of frames to form a data set in the form of pictures; perform smoke rendering on the obtained laparoscope smokeless images, and synthesize paired smoky images to obtain a synthetic data set containing the smokeless images and the smoky images

Input the smokeless images into a conditional diffusion model for forward noise addition, and continuously add noise until the smokeless images are completely noised to obtain a series of noisy images

Input the smoky images into a smoke sensing module to obtain smoke concentration and position information, then train a neural network through the series of noisy images, and perform reverse denoising using the trained neural network; continuously perform reverse denoising on the completely noised images until clear smokeless images are outputted

Optimize a de-smoking model through a multi-task strategy, and accelerate the model to generate smoke removal images with the skip sampling strategy

FIG. 1

METHOD, SYSTEM, AND DEVICE FOR REMOVING SMOKE FROM LAPAROSCOPE IMAGES BASED ON CONDITIONAL DIFFUSION MODEL

CROSS-REFERENCE TO RELATED APPLICATION

This application claims the priority benefit of Chinese application serial no. 202410115722.5, filed on Jan. 29, 2024. The entirety of the above-mentioned patent application is hereby incorporated by reference herein and made a part of this specification.

FIELD OF THE INVENTION

The present disclosure relates to the technical field of medical image processing, and particularly to a method, system, and device for removing smoke from laparoscope images based on a conditional diffusion model.

BACKGROUND OF THE INVENTION

In the laparoscopic surgery, using an instrument with electric cauterization capabilities may reduce the risk of bleeding, where the heating source is directly applied to the tissue for dissection. Doctors often use specialized tools such as electrotome, ultrasonic scalpels, and bipolar coagulation to achieve hemostasis during the surgery through high-temperature burning. Compared with the traditional surgery, the laparoscopic surgery has advantages such as smaller trauma, faster postoperative recovery, and smaller abdominal incision scars. However, a significant amount of smoke is often generated during this process. Generally, surgical smoke is generated when burning and cutting tissues during the laparoscopic surgery. This smoke is harmful not only to patients and surgeons but also reduces the surgical effects.

Currently, there are two main methods for removing smoke generated during the surgery, which are a machine-based method and an image processing-based method. During the surgery, doctors often use suction apparatuses and anti-fogging solutions to wipe the laparoscope lens to achieve the purpose of removing smoke. However, using the traditional machine-based method to remove smoke may cause the periodic interruption of the surgery, decreasing the efficiency of the surgery. The image processing-based smoke removal method includes traditional algorithms and deep learning algorithms. In traditional tasks of removing smoke from images, some prior-based physical models have been extensively studied and applied. Common physical models for smoke removal tasks include atmospheric scattering models, dark channel prior (DCP), color line prior, gradient channel prior, and so on.

Traditional models are mostly suitable for smoke removal tasks. However, the smoke generated during the laparoscopic surgery differs significantly from smoke produced in nature. The smoke generated during the surgery is often non-uniform and highly variable. Therefore, traditional single models cannot be completely suitable for smoke removal tasks in surgery. Additionally, the complex structures and texture information in surgical images require the models for laparoscopic smoke removal tasks to possess strong learning capabilities. Therefore, the present application proposes a method, system, and device for removing smoke from laparoscope images based on a conditional diffusion model.

SUMMARY OF THE INVENTION

Aiming at the shortcomings of the related art, the present disclosure provides a method, system, and device for removing smoke from laparoscope images based on a conditional diffusion model. In the present disclosure, the algorithm is embedded in a laparoscopic device and may solve the problem of blurred vision caused by smoke interference during the laparoscopic surgery.

The technical solutions of the present disclosure for solving the technical problems are as follows.

The present disclosure provides a method for removing smoke from laparoscope images based on a conditional diffusion model, specifically including the following steps:

step 1) segmenting a video of a laparoscopic surgery according to the number of frames to form a data set in the form of pictures; performing smoke rendering on the obtained laparoscope smokeless images, and synthesizing paired smoky images to obtain a synthetic data set containing the smokeless images and the smoky images;

step 2) inputting the smokeless images into the conditional diffusion model for forward noise addition, and continuously adding noise until the smokeless images are completely noised to obtain a series of noisy images;

step 3) inputting the smoky images into a smoke sensing module to obtain smoke concentration and position information, then training a neural network through the series of noisy images, and performing reverse denoising using the trained neural network; continuously performing reverse denoising on the completely noised images obtained in the step 2) until clear smokeless images are outputted; and step 4) optimizing a smoke removal model through a multi-loss function fusion strategy, and accelerating the model to generate smoke removal images using a skip sampling strategy.

A specific operation of the step 1) is as follows: segmenting the video of the laparoscopic surgery according to the number of frames to form the data set in the form of pictures; performing smoke rendering on the segmented laparoscope smokeless images using Blender rendering software, and synthesizing the paired smoky images; dividing synthetic smoky images into three smoke images with different levels of concentration, i.e., light smoke images, moderate smoke images, and heavy smoke image; and finally obtaining the smokeless images and the synthetic smoky images.

A specific operation of the step 2) is as follows: inputting the smokeless images captured by a laparoscope into the conditional diffusion model for forward noise addition, where an added noise variance is $\beta_t$; the noise addition process follows a Markov chain, and a noise-added image is recorded as $x_t$; and performing noise addition on inputted smokeless images T times until the smokeless images are completely noised to obtain the series of noisy images $\{x_1, x_2, \ldots, x_t, \ldots, x_T\}$, where $x_t$ represents a noise image obtained by performing a t-th noise addition, and $x_T$ represents a noise image obtained by performing a T-th noise addition;

an equation for the forward noise addition process is as follows:

$$x_t = \sqrt{1-\beta_t}\, x_{t-1} + \sqrt{\beta_t}\, \varepsilon,\ \varepsilon \sim N(0, I),$$

where ε represents noise, N represents a standard normal Gaussian distribution, I represents an identity matrix, and $x_{t-1}$ represents a noise image obtained by performing a t−1-th noise addition.

A specific operation of the step 3) is as follows: inputting the smoky images in the synthetic data set into the smoke sensing module to obtain smoke mask information and DCP information; taking the series of noisy images in the step 2) as labels for reverse training, where the reverse training process of each label is carried out through a U-Net network with the addition of a feature frequency compensation module FCB to jointly complete the training of the U-Net network; taking guidance images and the series of noisy images as inputs of the reverse training to train the U-Net network, the guidance images including the smokeless images and the synthetic smoky images in the synthetic data set; and finally, performing reverse denoising using the trained neural network, taking the smoke mask information and the DCP information as condition information to guide the reverse denoising process, and continuously performing denoising on the inputted completely noised images finally obtained in the step 2) until clear laparoscope smokeless images are obtained.

The smoke sensing module includes a smoke mask segmentation module and a DCP module, performing smoke segmentation and smoke concentration information extraction on the inputted smoky images, respectively;

minimum values in three channels of R, G, and B are taken to form a grayscale image, and then minimum value filtering is performed to obtain a dark channel in the DCP module; then, a network acquires smoke distribution and concentration information in the smoke images through the DCP, and the obtained smoke information is used as condition information to guide the reverse denoising in the diffusion model to generate related smokeless images;

related calculation equations are as follows:

$$M_c(F)=\sigma(MLP(AvgPool(F))+MLP(MaxPool(F))),$$

$$M_s(F)=\sigma(f^{7\times 7}([AvgPool(F);MaxPool(F)])),$$

$$F'=M_s\odot(M_c\odot F),$$

where $M_c(F)$ represents channel attention, $M_s(F)$ represents spatial attention, F represents a depth feature, σ represents a sigmoid activation function, AvgPool represents average pooling, MaxPool represents maximum pooling, MLP represents an activation function, $f^{7\times 7}$ represents a convolution operation of a 7*7 filter, [•, •] represents connection of feature maps, ⊙ represents element multiplication, and F' represents a feature map.

The feature frequency compensation module FCB includes a plurality of convolution filters, and bandwidth of these filters covers mid- and high-frequency components that are difficult to capture in the network; the calculation of the feature frequency compensation module FCB is as follows:

$$f_{k,\sigma}=G_{k\times k}^{\sigma}*f, k\in\{3,5,7,9\ldots\},$$

where $G_{k\times k}^{\sigma}$ represents a two-dimensional Gaussian kernel having a mean value of σ and a size of k, f represents an inputted feature value, and $f_{k,\sigma}$ represents a convolution output through the two-dimensional Gaussian kernel; four Gaussian kernels having sizes of 3, 5, 7, and 9 are selected for filtering, and a filter is obtained after making a difference between two Gaussian kernels, which is calculated and expressed by an equation as:

$$f_k'=\{f_k',f_3',f_5',f_7',f_9'\}=\{f_3f-f_3,f_3-f_5,f_5-f_7,f_7-f_9\},$$

where $f_k'$ represents an output after filtering, $f_9'$ represents frequency information after being filtered by the Gaussian kernel having a size of 9, $f_7'$ represents frequency information after being filtered by the Gaussian kernel having a size of 7, $f_5'$ represents frequency information after being filtered by the Gaussian kernel having a size of 5, and $f_3'$ represents frequency information after being filtered by the Gaussian kernel having a size of 3;

filtering of different frequency bands is then realized by selecting different Gaussian kernels, and $f_5'$ is weighted and summarized as follows:

$$\bar{f}=<W, f_k'>=W_1 f_k'+W_2 f_3'+W_3 f_5'+W_4 f_7'+W_5 f_9',$$

where $W=[W_1, W_2, W_3, W_4, W_5]$ represents a weight of trainable learning, and $\bar{f}$ represents an output after being weighted and summarized.

A specific operation of the step 4) is as follows: an $L_1$ loss equation is as follows:

$$L_1 = E_{(I,X)}E_{\varepsilon\sim N(0,1),\beta_t}\|f_\theta(I, x_t, \beta_t) - \varepsilon\|_1^1,$$

where $L_1$ represents a mean absolute error, $f_\theta$ represents the trained neural network, I represents an inputted smoky image, smoke mask image, and smoke density image as the condition information, ε represents noise obeying a normal Gaussian distribution, $x_t$ represents a t-th noise-added noise image, N represents a sum of pixels of an input image, E represents a weighted average operation, and X represents a noise-containing smokeless image;

an equation for a dark channel loss $L_{dcp}$ is as follows:

$$L_{dcp} = \frac{1}{N}\sum_x\left[I_{cp}^{dark}(x) - \tilde{I}_{cp}^{dark}(x)\right]^2,$$

where $I_{cp}^{dark}(x)$ and $\tilde{I}_{cp}^{dark}(x)$ represent the DCP, x represents one pixel in the input image, and N represents the sum of pixels of the input image; the input image refers to the inputted smoky image, smoke mask image, and smoke density image as the condition information I;

an equation for a contrast enhancement loss $L_{ce}$ is as follows:

$$L_{ce}=abs(\ln(CEF)^{-1}),$$

where CEF represents a contrast enhancement factor, and abs represents an operation of taking an absolute value.

The present disclosure also provides a system for removing smoke from laparoscope images based on a conditional diffusion model, including processing instruction modules configured to perform the steps of the method for removing smoke from laparoscope images based on a conditional diffusion model.

The present disclosure also provides an electronic device for removing smoke from laparoscope images based on a conditional diffusion model, including a processor and a memory storing a computer program, where the processor, when executing the computer program, implements the steps of the method for removing smoke from laparoscope images based on a conditional diffusion model.

BRIEF DESCRIPTION OF THE DRAWINGS

The accompanying drawings, which are intended to provide a further understanding of the present disclosure and constitute a part of this specification, illustrate the present disclosure together with the embodiments of the present disclosure and do not limit the present disclosure.

FIG. 1 is a schematic flowchart of a method of the present disclosure.

DETAILED DESCRIPTION OF THE EMBODIMENTS

Specific details of the present disclosure are further set forth in the following description for a full understanding of the present disclosure. The terms used in the specification in the present disclosure are for the purpose of illustrating the advantages and features of the present disclosure only, and are not intended to limit the present disclosure.

Figure 2:
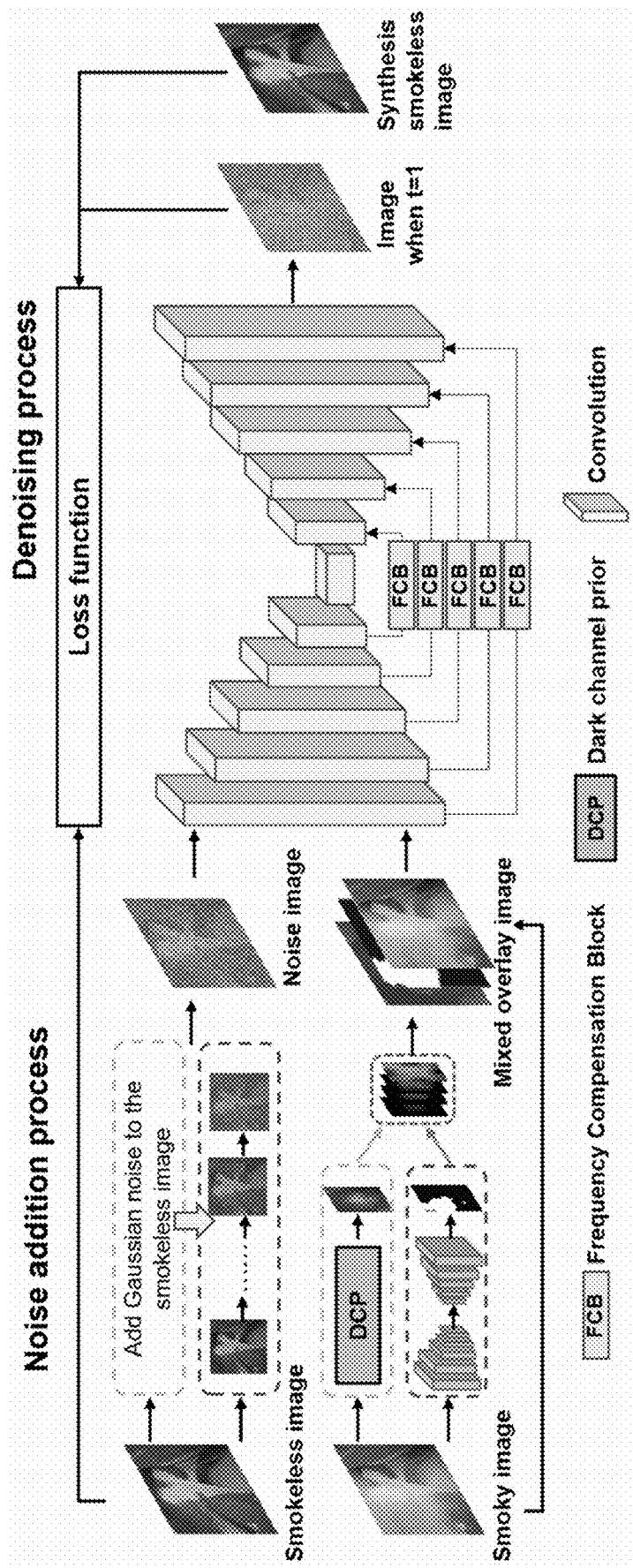
FIG. 2 is a general framework diagram of a method of the present disclosure.
Figure 3:
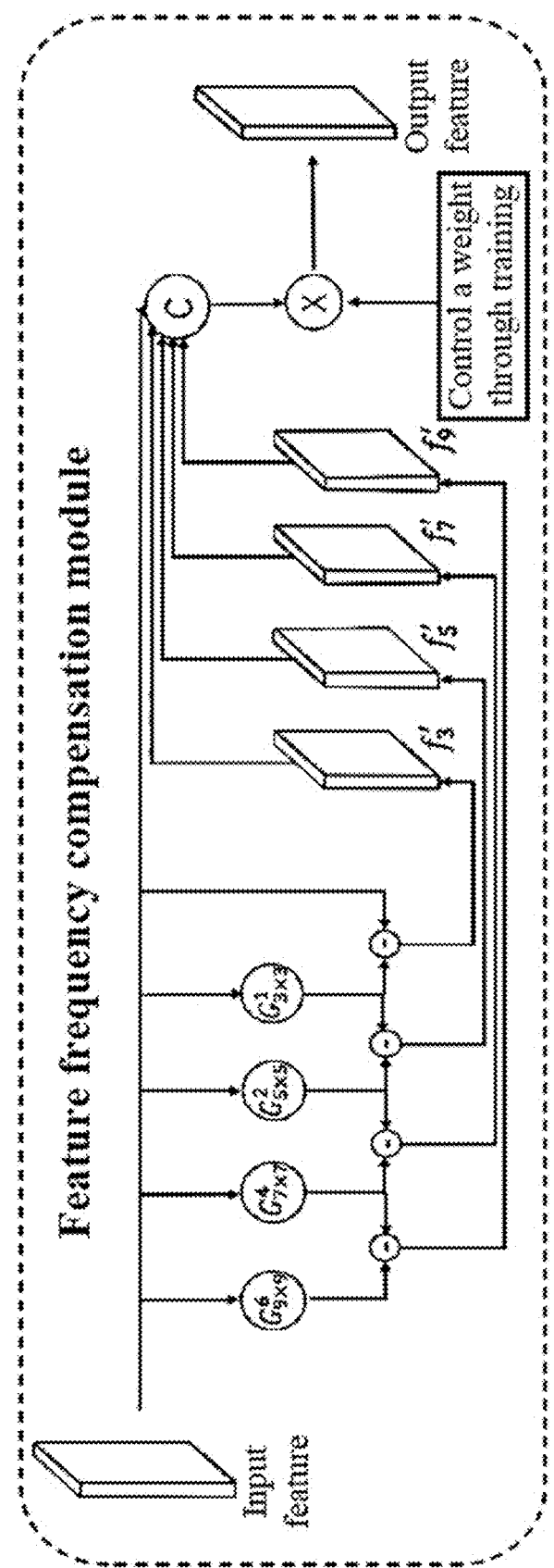
FIG. 3 is a schematic diagram of a feature frequency compensation module of the present disclosure.

Embodiment 1: as shown in FIGS. 1 to 3, a method for removing smoke from laparoscope images based on a conditional diffusion model is provided.

The present disclosure provides a method for removing smoke from laparoscope images based on a conditional diffusion model, specifically including the following steps:

step 1) segmenting a video of a laparoscopic surgery according to the number of frames to form a data set in the form of pictures; performing smoke rendering on the obtained laparoscope smokeless images, and synthesizing paired smoky images to obtain a synthetic data set containing the smokeless images and the smoky images;

step 2) inputting the smokeless images into the conditional diffusion model for forward noise addition, and continuously adding noise until the smokeless images are completely noised to obtain a series of noisy images;

step 3) inputting the smoky images into a smoke sensing module to obtain smoke concentration and position information, then training a neural network through the series of noisy images, and performing reverse denoising using the trained neural network; continuously performing reverse denoising on the completely noised images obtained in step 2) until clear smokeless images are outputted; and step 4) optimizing a smoke removal model through a multi-loss function fusion strategy, and accelerating the model to generate smoke removal images using a skip sampling strategy.

In a specific implementation, a specific operation of the step 1) is as follows: segmenting the video of the laparoscopic surgery according to the number of frames to form the data set in the form of pictures; performing smoke rendering on the segmented laparoscope smokeless images using Blender rendering software, and synthesizing the paired smoky images; dividing synthetic smoky images into three smoke images with different levels of concentration, i.e., light smoke images, moderate smoke images, and heavy smoke image; and finally obtaining the smokeless images and the synthetic smoky images.

In a specific implementation, a specific operation of the step 2) is as follows: inputting the smokeless images captured by a laparoscope into the conditional diffusion model for forward noise addition, where an added noise variance is $\beta_t$; the noise addition process follows a Markov chain, and a noise-added image is recorded as $\beta_t$; and performing noise addition on inputted smokeless images T times until the smokeless images are completely noised to obtain the series of noisy images $\{x_1, x_2, \ldots, x_t, \ldots, x_T\}$, where x represents a noise image obtained by performing a t-th noise addition, and $x_T$ represents a noise image obtained by performing a T-th noise addition.

An equation for the forward noise addition process is as follows:

$$x_t = \sqrt{1-\beta_t}\, x_{t-1} + \sqrt{\beta_t}\,\varepsilon,\ \varepsilon \sim N(0, I),$$

where ε represents noise, N represents a standard normal Gaussian distribution, I represents an identity matrix, and $x_{t-1}$ represents a noise image obtained by performing a t−1-th noise addition.

In a specific implementation, a specific operation of the step 3) is as follows: inputting the smoky images in the synthetic data set into the smoke sensing module to obtain smoke mask information and DCP information; taking the series of noisy images in the step 2) as labels for reverse training, where the reverse training process of each label is carried out through a U-Net network with the addition of a feature frequency compensation module FCB to jointly complete the training of the U-Net network; taking guidance images and the series of noisy images as inputs of the reverse training to train the U-Net network, the guidance images including the smokeless images and the synthetic smoky images in the synthetic data set; and finally, performing reverse denoising using the trained neural network, taking the smoke mask information and the DCP information as condition information to guide the reverse denoising process, and continuously performing denoising on the inputted completely noised images finally obtained in the step 2) until clear laparoscope smokeless images are obtained.

However, the feature frequency compensation module includes convolution filters, and bandwidth of these filters covers mid- and high-frequency components that are difficult to capture in the network. The back diffusion process of the diffusion model needs to train a neural network to predict the distribution of noise, then denoising can be performed on the inputted noise image, and a clear laparoscope smokeless image without noise is gradually obtained. However, in the frequency range, when gradually adding noise to the image, the high-frequency component in the image increases, and the power spectrum in the natural image will decrease with the increase of the frequency. However, the Gaussian noise follows a uniform power spectrum density, and a deep neural network prefers a smooth function and tends to learn low-frequency information. In the training process, an effective objective function of the deep neural network tends to be closer to the low frequency. That is, the deep neural network learns the low-frequency information first and puts the learning of high-frequency information in the late training stage. Because an initial input of the back diffusion process of the diffusion model is a noise image, the high-frequency information is rich, but in the process of the neural network learning the noise distribution, the noise gradually decreases so that the efficiency of the neural network learning a noise vector will decrease, and the learning of the medium and high-frequency information is often not thorough.

In a specific implementation, the smoke sensing module includes a smoke mask segmentation module and a DCP module, for smoke segmentation and smoke concentration information extraction on the inputted smoky images, respectively.

Minimum values in three channels of R, G, and B are taken to form a grayscale image, and then minimum value filtering is performed to obtain a dark channel in the DCP module. Then, a network acquires smoke distribution and concentration information in the smoke images through the DCP, and the obtained smoke information is used as condition information to guide the reverse denoising in the diffusion model to generate related smokeless images.

The DCP holds that in most non-sky local areas, there are some pixels that have very low values in at least one color channel, approaching 0. The dark channel is actually obtained by taking the minimum values in three channels of R, G, and B to form a grayscale image, and then performing minimum value filtering. The network acquires the smoke distribution and concentration information in the smoke images through the DCP, and the obtained smoke information is used as the condition information to guide the diffusion model to generate the related smokeless images. A smoke segmentation network follows a U-shaped structure of encoder-decoder. Five convolution blocks are applied in each of the encoder stage and the decoder stage, and a lightweight attention mechanism module CBAM is added after the first four convolution blocks of the decoder, which overcomes the limitations of traditional convolution neural networks (CNNs) in processing different scales, shapes, and directions of information. Channel attention and spatial attention are introduced into the CNN to improve the perception of the model, thereby improving the performance without increasing the complexity of the network. The CBAM module may help the smoke segmentation network to better capture smoke feature information in the smoke image. For each intermediate feature map, the CBAM module acquires attention maps along two independent dimensions, i.e., a channel and a space, and then multiplies the attention maps with an input feature map to perform adaptive feature optimization. A residual connection is used, which may help to better transfer information between the encoder and the decoder and may directly transfer the features extracted from the encoder to the decoder, thus helping to retain the detailed information of the input image.

Related calculation equations are as follows:

$$M_c(F)=\sigma(MLP(\text{AvgPool}(F))+MLP(\text{MaxPool}(F))),$$

$$M_s(F)=\sigma(f^{7\times 7}([\text{AvgPool}(F);\text{MaxPool}(F)])),$$

$$F'=M_c\odot(M_c\odot F),$$

where $M_c(F)$ represents channel attention, $M_s(F)$ represents spatial attention, F represents a depth feature, $\sigma$ represents a sigmoid activation function, AvgPool represents average pooling, MaxPool represents maximum pooling, MLP represents an activation function, $f^{7\times 7}$ represents a convolution operation of a 7*7 filter, [•, •] represents connection of feature maps, $\odot$ represents element multiplication, and F' represents a feature map.

The smoke mask segmentation module follows the U-shaped structure of encoder-decoder. The encoder part is built based on a fictional VGG16 network, and a fully connected layer of the VGG16 is removed to reduce the number of trainable parameters. The decoder part is inversely proportional to the encoder. In order to obtain multi-scale features and retain detailed spatial information, a jump connection is added between the encoding stage and the decoding stage. In addition, before training the diffusion model, the smoke mask segmentation module is independently trained, and channel and spatial attention are added after each set of convolution blocks to recalibrate the feature maps by focusing on important features.

The DCP holds that in most non-sky local areas, there are some pixels that have very low values in at least one color channel, approaching 0. The dark channel is actually obtained by taking the minimum values in three channels of R, G, and B to form a grayscale image, and then performing minimum value filtering. The network acquires the smoke distribution and concentration information in the smoke images through the DCP, and the obtained smoke information is used as the condition information to guide the diffusion model to generate the related smokeless images. A smoke segmentation network follows a U-shaped structure of encoder-decoder. Five convolution blocks are applied in each of the encoder stage and the decoder stage, and a lightweight attention mechanism module CBAM is added after the first four convolution blocks of the decoder, which overcomes the limitations of traditional CNNs in processing different scales, shapes, and directions of information. Channel attention and spatial attention are introduced into the CNN to improve the perception of the model, thereby improving the performance without increasing the complexity of the network. The CBAM module may help the smoke segmentation network to better capture smoke feature information in the smoke image. For each intermediate feature map, the CBAM module acquires attention maps along two independent dimensions, i.e., a channel and a space, and then multiplies the attention maps with an input feature map to perform adaptive feature optimization. A residual connection is used, which may help to better transfer information between the encoder and the decoder and may directly transfer the features extracted from the encoder to the decoder, thus helping to retain the detailed information of the input image.

In a specific implementation, the feature frequency compensation module FCB includes a plurality of convolution filters, and bandwidth of these filters covers mid- and high-frequency components that are difficult to capture in the network. The calculation of the feature frequency compensation module FCB is as follows:

$$f_{k,\sigma}=G_{k\times k}{}^{\sigma}*f,\ k\in\{3,5,7,9\ldots\},$$

where $G_{k\times k}{}^{\sigma}$ represents a two-dimensional Gaussian kernel having a mean value of $\sigma$ and a size of k, and values of $\sigma$ are 6, 4, 2, and 1; the passed Gaussian kernels are: a Gaussian kernel $G_{9\times 9}{}^{6}$, having a size of 9 and a standard deviation of 6, a Gaussian kernel $G_{7\times 7}{}^{4}$ having a size of 7 and a standard deviation of 4, a Gaussian kernel $G_{5\times 5}{}^{2}$ having a size of 5 and a standard deviation of 2, and a Gaussian kernel $G_{3\times 3}{}^{1}$, having a size of 3 and a standard deviation of 1; f represents an inputted feature value, $f_{k,\sigma}$ represents a convolution output through the two-dimensional Gaussian kernel; four Gaussian kernels having sizes of 3, 5, 7, and 9 are selected for filtering, and a filter is obtained after making a difference between two Gaussian kernels, which is calculated and expressed by an equation as:

$$f_k'=\{f_k', f_3', f_5', f_7', f_9'\}=\{f_1-f_3, f_3-f_5, f_5-f_7, f_7-f_9\},$$

where $f_k'$ represents an output after filtering, $f_9'$ represents frequency information after being filtered by the Gaussian kernel having a size of 9, $f_7'$ represents frequency information after being filtered by the Gaussian kernel having a size of 7, $f_5'$ represents frequency information after being filtered by the Gaussian kernel having a size of 5, and $f_3'$ represents frequency information after being filtered by the Gaussian kernel having a size of 3.

Filtering of different frequency bands is then realized by selecting different Gaussian kernels, and $f_5'$ is weighted and summarized as follows:

$$\bar{f}=<W, f_k'> = W_1 f_k' + W_2 f_3' + W_3 f_5' + W_4 f_7' + W_5 f_9',$$

where $W=[W_1, W_2, W_3, W_4, W_5]$ represents a weight of trainable learning, and $\bar{f}$ represents an output after being weighted and summarized.

In a specific implementation, a specific operation of the step 4) is as follows.

An $L_1$ loss equation is as follows:

$$L_1 = E_{(I,X)} E_{\varepsilon \sim N(0,1), \beta_t} \|f_\theta(I, x_t, \beta_t) - \varepsilon\|_1^1,$$

where $L_1$ represents a mean absolute error, $f_\theta$ represents the trained neural network, I represents an inputted smoky image, smoke mask image, and smoke density image as the condition information, $\varepsilon$ represents noise obeying a normal Gaussian distribution, $x_t$ represents a t-th noise-added noise image, N represents a sum of pixels of an input image, E represents a weighted average operation, and X represents a noise-containing smokeless image.

An equation for a dark channel loss $L_{dcp}$ is as follows:

$$L_{dcp} = \frac{1}{N} \sum_x \left[I_{cp}^{dark}(x) - \tilde{I}_{cp}^{dark}(x)\right]^2,$$

where $I_{cp}^{dark}(x)$ and $\tilde{I}_{cp}^{dark}(x)$ represent the DCP, x represents one pixel in the input image, and N represents the sum of pixels of the input image; the input image refers to the inputted smoky image, smoke mask image, and smoke density image as the condition information I.

An equation for a contrast enhancement loss $L_k$ is as follows:

$$L_{ce}=\text{abs}(\ln(\text{CEF})^{-1}),$$

where CEF represents a contrast enhancement factor, and abs represents an operation of taking an absolute value.

Embodiment 2: a system for removing smoke from laparoscope images based on a conditional diffusion model is provided, including processing instruction modules configured to perform the steps of the method for removing smoke from laparoscope images based on a conditional diffusion model.

Embodiment 3: an electronic device for removing smoke from laparoscope images based on a conditional diffusion model is provided, including a processor and a memory storing a computer program, where the processor, when executing the computer program, implements the steps of the method for removing smoke from laparoscope images based on a conditional diffusion model.

Embodiment 4: in this embodiment, a distributed learning method is adopted. The model is implemented in Python using a PyTorch framework, and all training is completed on NVIDIAGeForceRTX309024 GB and PyTorch1.7. An Adam optimizer is adopted to minimize the objective function, and the learning rate is set to 0.0001. In order to deal with the video memory problem of hardware devices, the image input is modified as 256×256, the batch is set to 4, the time step of the diffusion model is set to 2000, and the volume size is set to 1.

Figure 4:
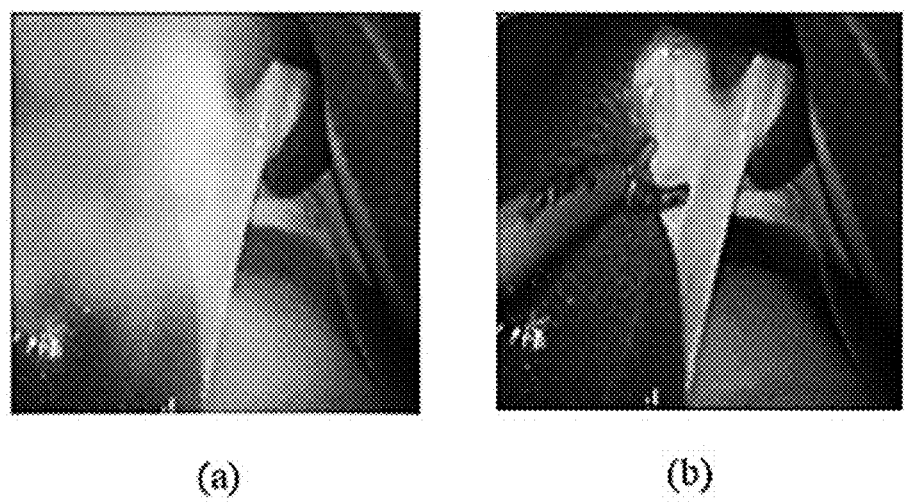
FIG. 4 is a schematic diagram of the smoke removal effect of the present disclosure, where (a) is a smoky image, and (b) is a smoke removal image.

Three indicators of peak signal-to-noise ratio (PSNR), structural similarity index measure (SSIM), and CIEDE-2000 color difference equation are adopted to quantify the model in the present disclosure and the other fourteen models in the laparoscopic data set. The larger the PSNR value, the higher the quality of the image, and the closer the SSIM is to 1, the smaller the difference between the images and the more similar. The closer the indicator of CIEDE-2000 used for measuring the color difference is to 0, the smaller the color difference between the synthesized image and the real image. The method of the present disclosure is compared with other model methods SSIMPAN, DS-Cycle-GAN, De-smokeGCN, CG-ASM, PAN, CGAN-DC, MARS-GAN, Cycle-Dehaze, AODNet, MPR-Net, Dehaze-Net, DCP, FFA-Net, Pix2Pix, and CycleGAN, and the best results are obtained. As shown in Table 1, the model of the present disclosure is superior to the compared 15 smoke removal models in the three indicators of PSNR, SSIM, and CIEDE-2000. FIG. 4 is a smoke removal effect diagram under the method of the present disclosure, where the left side shows a smoky image, and the right side shows a smoke removal image. From the comparison in FIG. 4, it can be seen that the smoke removal effect of the present disclosure is very significant.

TABLE 1

Comparison of indicators between model in this method and other models

| Method | FSNR | SSIM | CIEDE-2000 |
| --- | --- | --- | --- |
| SSIM-PAN | 23.358 ± 1.684 | 0.847 ± 0.049 | 6.853 ± 2.720 |
| DS-CycleGAN | 26.532 ± 1.921 | 0.870 ± 0.086 | 5.264 ± 2.305 |
| De-smote GCN | 26.980 ± 1.422 | 0.897 ± 0.045 | 4.725 ± 3.258 |
| CG-ASM | 26.794 ± 1.476 | 0.873 ± 0.096 | 5.743 ± 2.760 |
| PAN | 22.452 ± 1.603 | 0.828 ± 0.037 | 8.326 ± 2.861 |
| CGAN-DC | 26.634 ± 1.372 | 0.880 ± 0.037 | 5.850 ± 2.480 |
| Cycle-Dehaze | 25.430 ± 1.762 | 0.886 ± 0.047 | 8.320 ± 2.450 |
| AODNet | 18.655 ± 1.471 | 0.812 ± 0:038 | 10.135 ± 3.752 |
| MPR-Net | 26.713 ± 1.715 | 0.904 ± 0.025 | 4.883 ± 2.140 |
| Dehaze-Net | 20.591 ± 2.730 | 0.775 ± 0.028 | 12.326 ± 4.380 |
| DCP | 15.747 ± 1.380 | 0.728 ± 0.046 | 12.450 ± 4.520 |
| FFA-Net | 22.794 ± 2.143 | 0.851 ± 0.084 | 6.640 ± 1.732 |
| Pix2Pix | 23.735 ± 2.063 | 0.829 ± 0.056 | 7.265 ± 2.457 |
| CycleGAN | 23.558 ± 2.364 | 0.864 ± 0.072 | 6.750 ± 1,640 |
| MARS-GAN | 27.821 ± 1.825 | 0.918 ± 0.025 | 4.055 ± 1.860 |
| Ours Proposed | 28.314 ± 1.921 | 0.929 ± 0.032 | 3.994 ± 1.901 |

The effects provided in the summary of the present disclosure are merely those of the embodiments, but not all the effects of the present disclosure. The beneficial effects of the present disclosure are as follows.

The safety of the surgical procedure is improved. Smoke will seriously affect the doctor's observation of the patient's tissue during the surgery, which may lead to inaccurate operations. A laparoscopic smoke removal algorithm can effectively reduce the interference of smoke on the vision and improve the safety and accuracy of the surgery.

The experience of doctors and patients is improved. Clear vision may make the doctor perform better while reducing the surgery time and improving the surgery efficiency. Thus, patients can get better treatment results during the surgery.

The surgical risk is reduced. The application of the laparoscopic smoke removal algorithm may reduce the risk of surgical complications and reduce surgical accidents caused by smoke interference.

The medical level is improved. The application of this algorithm will help to improve the technical level of medical devices, provide doctors with better working conditions, and provide patients with safer and more efficient treatment services.

Although specific implementations of the present disclosure have been described above with reference to the accompanying drawings, it is not intended to limit the scope of the present disclosure. On the basis of the technical solutions of the present disclosure, various modifications or changes can be made by a person skilled in the art without involving any inventive effort, and these modifications or changes fall within the scope of the present disclosure.

What is claimed is:

1. A method for removing smoke from laparoscope images based on a conditional diffusion model, comprising the following steps:
   1) segmenting a video of a laparoscopic surgery according to the number of frames to form a data set in the form of pictures; performing smoke rendering on the obtained laparoscope smokeless images, and synthesizing paired smoky images to obtain a synthetic data set containing the smokeless images and the smoky images;
   2) inputting the smokeless images into the conditional diffusion model for forward noise addition, and continuously adding noise until the smokeless images are completely noised to obtain a series of noisy images, wherein a specific operation of the step 2) is as follows: inputting the smokeless images captured by a laparoscope into the conditional diffusion model for forward noise addition, wherein an added noise variance is $\beta_t$; the noise addition process follows a Markov chain, and a noise-added image is recorded as $x_t$; and performing noise addition on inputted smokeless images T times until the smokeless images are completely noised to obtain the series of noisy images $\{x_1, x_2, \ldots, x_t, \ldots, x_T\}$, wherein $x_t$ represents a noise image obtained by performing a t-th noise addition, and $x_T$ represents a noise image obtained by performing a T-th noise addition;
   an equation for the forward noise addition process is as follows:

$$x_t = \sqrt{1-\beta_t}\, x_{t-1} + \sqrt{\beta_t}\, \varepsilon,\ \varepsilon \sim N(0, I),$$

wherein $\varepsilon$ represents noise, N represents a standard normal Gaussian distribution, I represents an identity matrix, and $x_{t-1}$ represents a noise image obtained by performing a t−1-th noise addition;
   3) inputting the smoky images into a smoke sensing module to obtain smoke concentration and position information, then training a neural network through the series of noisy images, and performing reverse denoising using the trained neural network; continuously performing reverse denoising on the completely noised images obtained in the step 2) until clear smokeless images are outputted,
   wherein a specific operation of the step 3) is as follows: inputting the smoky images in the synthetic data set into the smoke sensing module to obtain smoke mask information and dark channel prior (DCP) information; taking the series of noisy images in the step 2) as labels for reverse training, wherein the reverse training process of each label is carried out through a U-Net network with the addition of a feature frequency compensation module FCB to jointly complete the training of the U-Net network; taking guidance images and the series of noisy images as inputs of the reverse training to train the U-Net network, the guidance images comprising the smokeless images and the synthetic smoky images in the synthetic data set; and finally, performing reverse denoising using the trained neural network, taking the smoke mask information and the DCP information as condition information to guide the reverse denoising process, and continuously performing denoising on the inputted completely noised images finally obtained in the step 2) until clear laparoscope smokeless images are obtained;
   the smoke sensing module comprises a smoke mask segmentation module and a DCP module, for smoke segmentation and smoke concentration information extraction on the inputted smoky images, respectively;
   minimum values in three channels of R, G, and B are taken to form a grayscale image, and then minimum value filtering is performed to obtain a dark channel in the DCP module; then, a network acquires smoke distribution and concentration information in the smoke images through the DCP, and the obtained smoke information is used as condition information to guide the reverse denoising in the diffusion model to generate related smokeless images;
   related calculation equations are as follows:

$$M_c(F) = \sigma(MLP(\text{AvgPool}(F)) + MLP(\text{MaxPool}(F))),$$

$$M_s(F) = \sigma(f^{7\times 7}([\text{AvgPool}(F); \text{MaxPool}(F)])),$$

$$F' = M_c \odot (M_c \odot F),$$

wherein $M_c(F)$ represents channel attention, $M_s(F)$ represents spatial attention, F represents a depth feature, $\sigma$ represents a sigmoid activation function, AvgPool represents average pooling, MaxPool represents maximum pooling, MLP represents an activation function, $f^{7\times 7}$ represents a convolution operation of a 7+7 filter, [•, •] represents connection of feature maps, (represents element multiplication, and F' represents a feature map;
   the feature frequency compensation module FCB comprises a plurality of convolution filters, and bandwidth of these filters covers mid- and high-frequency components that are difficult to capture in the network; the calculation of the feature frequency compensation module FCB is as follows:

$$f_{k,\sigma} = G_{k\times k}^{\sigma} * f,\ k \in \{3, 5, 7, 9 \ldots\},$$

wherein $G_{k\times k}^{\sigma}$ represents a two-dimensional Gaussian kernel having a mean value of $\sigma$ and a size of k, f represents an inputted feature value, and $f_{k,\sigma}$ represents a convolution output through the two-dimensional Gaussian kernel; four Gaussian kernels having sizes of 3, 5, 7, and 9 are selected for filtering, and a filter is obtained after making a difference between two Gaussian kernels, which is calculated and expressed by an equation as:

$$f_k' = \{f_k', f_3', f_5', f_7', f_9'\} = \{f_1-f_3, f_3-f_5, f_5-f_7, f_7-f_9\},$$

wherein $f_k'$ represents an output after filtering, $f_9'$ represents frequency information after being filtered by the Gaussian kernel having a size of 9, $f_7'$ represents frequency information after being filtered by the Gaussian kernel having a size of 7, $f_5'$ represents frequency information after being filtered by the Gaussian kernel having a size of 5, and $f_3'$ represents frequency information after being filtered by the Gaussian kernel having a size of 3;

filtering of different frequency bands is then realized by selecting different Gaussian kernels, and f is weighted and summarized as follows:

$$\bar{f} = <W, f_k'> = W_1 f_1' + W_2 f_3' + W_3 f_5' + W_4 f_7' + W_5 f_9',$$

wherein $W=[W_1, W_2, W_3, W_4, W_5]$ represents a weight of trainable learning, and $\bar{f}$ represents an output after being weighted and summarized; and 4) optimizing a smoke removal model through a multi-loss function fusion strategy, and accelerating the model to generate smoke removal images using a skip sampling strategy.

2. The method for removing smoke from laparoscope images based on a conditional diffusion model according to claim 1, wherein a specific operation of the step 1) is as follows: segmenting the video of the laparoscopic surgery according to the number of frames to form the data set in the form of pictures; performing smoke rendering on the segmented laparoscope smokeless images using Blender rendering software, and synthesizing the paired smoky images; dividing synthetic smoky images into three smoke images with different levels of concentration, i.e., light smoke images, moderate smoke images, and heavy smoke image; and finally obtaining the smokeless images and the synthetic smoky images.

3. The method for removing smoke from laparoscope images based on a conditional diffusion model according to claim 2, wherein a specific operation of the step 4) is as follows:

an $L_1$ loss equation is as follows:

$$L_1 = E_{(I,X)} E_{\varepsilon \sim N(0,1), \beta_t} \|f_\theta(I, x_t, \beta_t) - \varepsilon\|_1^1,$$

wherein $L_1$ represents a mean absolute error, $f_\theta$ represents the trained neural network, I represents an inputted smoky image, smoke mask image, and smoke density image as the condition information, $\varepsilon$ represents noise obeying a normal Gaussian distribution, $x_t$ represents a t-th noise-added noise image, N represents a sum of pixels of an input image, E represents a weighted average operation, and X represents a noise-containing smokeless image;

an equation for a dark channel loss $L_{dcp}$ is as follows:

$$L_{dcp} = \frac{1}{N} \sum_x \left[ I_{cp}^{dark}(x) - \tilde{I}_{cp}^{dark}(x) \right]^2,$$

wherein $I_{cp}^{dark}(x)$ and $\tilde{I}_{cp}^{dark}(x)$ represent the DCP, x represents one pixel in the input image, and N represents the sum of pixels of the input image; the input image refers to the inputted smoky image, smoke mask image, and smoke density image as the condition information I;

an equation for a contrast enhancement loss $L_{ce}$ is as follows:

$$L_{ce} = \text{abs}(\ln(\text{CEF})^{-1}),$$

wherein CEF represents a contrast enhancement factor, and abs represents an operation of taking an absolute value.

4. An electronic device for removing smoke from laparoscope images based on a conditional diffusion model, comprising a processor and a memory storing a computer program, wherein the processor, when executing the computer program, implements the steps of the method for removing smoke from laparoscope images based on a conditional diffusion model according to claim 1.

5. An electronic device for removing smoke from laparoscope images based on a conditional diffusion model, comprising a processor and a memory storing a computer program, wherein the processor, when executing the computer program, implements the steps of the method for removing smoke from laparoscope images based on a conditional diffusion model according to claim 2.

6. An electronic device for removing smoke from laparoscope images based on a conditional diffusion model, comprising a processor and a memory storing a computer program, wherein the processor, when executing the computer program, implements the steps of the method for removing smoke from laparoscope images based on a conditional diffusion model according to claim 3.

* * * * *